United States Patent [19]  
Pitt

[11] Patent Number: 4,528,196  
[45] Date of Patent: Jul. 9, 1985

[54] CHELATING AGENTS FOR THE TREATMENT OF IRON OVERLOAD

[75] Inventor: Colin G. Pitt, Research Triangle Park, N.C.

[73] Assignee: The United States of America as represented by the Department of Health and Human Services, Washington, D.C.

[21] Appl. No.: 237,496

[22] Filed: Feb. 23, 1981

[51] Int. Cl.³ .................... C07C 101/30; C07C 31/24
[52] U.S. Cl. ........................................ 514/533; 560/39
[58] Field of Search ........................... 560/39; 424/309

[56] References Cited  
U.S. PATENT DOCUMENTS  
4,069,249 1/1978 Gaudette et al. .................. 562/448

OTHER PUBLICATIONS  
Pitt et al., J. Pharmacol. Exp. Ther., 208(1), pp. 12–18, (1979).

Primary Examiner—James H. Reamer  
Attorney, Agent, or Firm—John S. Roberts, Jr.

[57] ABSTRACT

The present invention consists of chelating agents for the treatment of iron overload and methods of using these agents in mammals such as mice and rats. These agents or compositions comprise diesters of dicarboxylic acids, which are phenolic derived and otherwise resemble ethylene and propylenediamine diacetic acids.

The acids are known as: HBED [N,N'-bis(2-hydroxybenzyl)ethylenediamine N,N-diacetic acid]; EHPG [ethylenediamine N,N'-bis(2-hydroxyphenylacetic acid)]; HBPD [N,N'- bis(2-hydoxybenzyl)propylenediamine-N,N'-diacetic acid]; HBHPD [N,N'- bis(2-hydroxybenzyl)-2-hydroxy-1,3-propylenediamine-N,N'-diacetic acid].

Mineral acid addition salts are also included in the spirit of this invention. Such salts as sulfuric, hydrochloric and nitric may be utilized.

In activity it has been found that the odd-numbered carbon atom esters, such a dimethyl and dipentyl, specially of HBED, are of highest activity, as well as the dipentyl ester of the HBPD. In summation, the HBED esters were found to have the highest activity of those esters studied.

5 Claims, No Drawings

CHELATING AGENTS FOR THE TREATMENT OF IRON OVERLOAD

The invention described herein was made in the course of work under a grant or award from the Department of Health and Human Services.

The purpose of this invention is to provide improved and orally effective iron chelating agents for the treatment of iron overload. For test purposes an intraperitoneal (IP) vehicle of administration is utilized in addition to the oral since with the laboratory animals it offers a better possibility for success.

BACKGROUND

Iron is stored in the body in the form of the protein complexes, ferritin and hemosiderin, and is transported in the plasma via the protein complex, transferrin. It has been estimated that, under normal physiological conditions, about a third to a half of transferrin's iron capacity is utilized. Iron overload leads to saturation of the transferrin and ferritin and results in toxicity as the excess iron leaves the bloodstream and accumulates in tissues. In principle, this condition can be successfully treated by administration of known iron chelating agent which remobilizes the deposited iron and permits its excretion. In practice, none of the chelating agents which have been evaluated to date have proved entirely satisfactory, suffering from poor gastrointestinal absorption (oral inactivity) and either low efficacy or undesirable side effects.

A review of the clinical usefulness of iron chelating agents presently employed in the treatment of iron overload has defined the properties of the ideal drug. In summary, the drug should be inexpensive, orally administrable, non-toxic, and resistant to degradation prior to efficient absorption via the gastrointestinal tract. Once absorbed, it must be dispersed through the body by the bloodstream and able to bind avidly to iron in competition with transferrin. It should not interfere with intracellular iron biochemistry; e.g., cellular respiration, and should be resistant to metabolic changes which impair its iron sequestering ability.

Given current knowledge of the kinetics and thermodynamics of iron binding in vitro, of iron metabolism in vivo, and the ability to prepare chelating agents which bind iron (III) more effectively than the natural iron transport and storage proteins, it would seem a simple task to develop a drug capable of quantitatively removing iron from the body. The fact that this has not yet been achieved is a reflection of the other factors which determine drug efficacy, specifically their bioavailability and biostability; additionally, the toxicity of some drugs has restricted their utility. The molecular features which influence the bioavailability and stability of iron chelators and effect oral activity by optimizing GI absorption are noted in the esters of the present invention.

Most information on the relative effectiveness of iron chelators has been obtained using one of two animal models to simulate the condition of iron overload. Both animal models utilize IP injections of heat damaged red cells to achieve overload. In one screen utilized here, with results reported in Table 1, rat is the test animal, drug administration and red cell transfusions are concurrent, and efficacy is measured by the iron excreted in the urine and feces. The second screen uses the mouse, drug administration is initiated after transfusions are complete, and efficacy is based on percent iron depleted from the liver and spleen, plus urinary iron excretion.

On the basis of several related considerations, efforts were focused on the synthesis of polydentate chelating agents derived from phenol. Multidenticity was achieved by combining this ligand with amino and carboxylic acid ligands. The present chelating agents were evaluated in vivo using a hypertransfused rat or mouse screen. Two compounds reproducibly showed greater activity than deferrioxamine B (DFB), the current drug of choice for treatment of iron overload. These were EHPG and HBED. Some of their analogs shown below were also active.

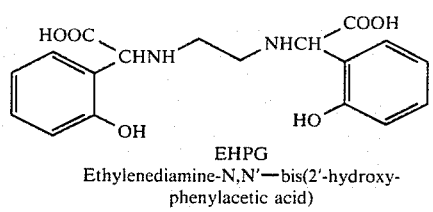

EHPG
Ethylenediamine-N,N'—bis(2'-hydroxyphenylacetic acid)

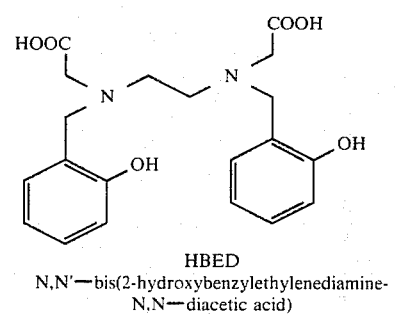

HBED
N,N'—bis(2-hydroxybenzylethylenediamine-N,N—diacetic acid)

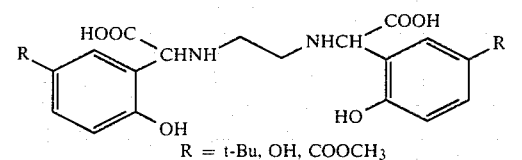

R = t-Bu, OH, COOCH$_3$

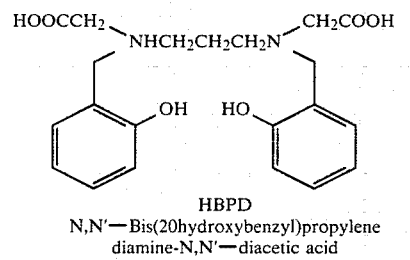

HBPD
N,N'—Bis(20hydroxybenzyl)propylene diamine-N,N'—diacetic acid

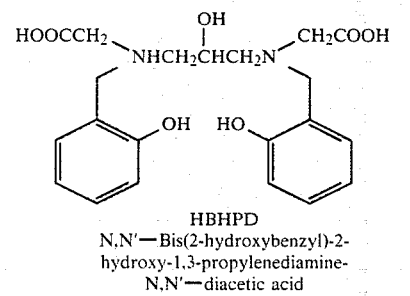

HBHPD
N,N'—Bis(2-hydroxybenzyl)-2-hydroxy-1,3-propylenediamine-N,N'—diacetic acid It was found that the alkyl esters of these dicarboxylic acids are very effective when administered orally. For example, the dimethyl and di-n-pentyl esters of HBED are more effective orally than is DFB administered I.P.

PRIOR ART STATEMENT

Patents already exist on the preparation of the EHPG, HBED and structurally related free carboxylic acids, these compounds being of value as the ferric chelates for the treatment of iron chlorosis in the plant kingdom.

Patents

U.S. Pat. No. 3,005,848 Knell et al (Geigy)—ethylenediamine derivatives containing aromatic rings.

U.S. Pat. No. 3,758,540 Martell—devoted to soluble iron (III) chelates of N-(2-hydroxybenzyl)substituted aminopolycarboxylic acid ligands useful in plant nutrition as a source of iron. Note at column 2 the disclosure of the specific compound N,N'-bis(2-hydroxybenzyl)-N,N'-ethylenediaminediacetic acid useful as a chelating agent.

U.S. Pat. No. 3,833,590 Dazzi (Ciba-Geigy)—chelates for the control of metal deficiency phenomena in biological systems which, as indicated, are the chelates useful for remedy of iron chlorosis in plants and the statement at column 1, line 45, "are used for the correction of metal-deficiency phenomena occurring in plants and mammals." Of course, the present invention is directed to remedying a surface of iron in lower animals and humans.

U.S. Pat. No. 4,116,991 Leneuf—hydroxy-containing agents for chelating metal ions and a process for preparing same.

U.S. Pat. No. 4,130,582 Petree et al (Ciba-Geigy)—preparation of phenolic ethylenediamine polycarboxylic acids.

Literature

Pitt and Gupta, "The Design and Synthesis of Chelating Agents for the Treatment of Iron Overload in Cooley's Anemia" in *Symposium on Development of Iron Chelators for Clinical Use*, Eds. Anderson and Hiller, DHEW Publication No. (NIH) 77-994, Bethesda, Md., pp. 137-174.

Pitt and Martell, "The Design of Chelating Agents for the Treatment of Iron Overload" in *Inorganic Chemistry in Biology and Medicine*, Ed. Martell, ACS Symposium Series, in press.

Cerami et al, "The Development of New Iron Chelating Drugs" in *Symposium on the Development of Iron Chelators for Clinical Use*, Eds. Anderson and Hiller, DHEW Publication No. (NIH) 77-994, Bethesda, Md., 1975, pp. 261-268.

Gralla, "Efforts to Develop a Bioassay System for Detecting Compounds Which Actively Deplete Iron Stores" in *Symposium on the Development of Iron Chelators for Clinical Use*, Eds. Anderson and Miller, DHEW Publication No. (NIH) 77-994, Bethesda, Md., 1975, pp. 229-254.

Pitt et al, *J. Pharmacol. Exp. Ther.*, 1979, 208(1), at page 15 teaches (Table 4) the naked disclosure of EHPG (EDHPA) dimethyl ester dihydrochloride.

EXPERIMENTAL RESULTS

Experimental results are shown in Table 1 below.

TABLE 1

Biological Activities of DFB and Derivatives of EHPG, HBED and Related Chelators Measured Using Rat Model of Iron Overload

| Compound | Route Admin. | LD$_{50}$ mg/kg | Relative Iron Excretion* Urine | Feces | Total |
|---|---|---|---|---|---|
| DFB | ip | 800 | 1 | 2 | 3 |
| EHPG | ip | 175 | 3 | 4 | 7 |
|  | po |  | 0 | 2 | 2 |
|  | po |  | 0 | 0 | 0 |
| EHPG, Dimethyl Ester | ip | 800 | 1 | 3 | 4 |
|  | po |  | 1 | 3 | 4 |
| Diethyl Ester | po | 800 | 1 | 1 | 2 |
| Dipropyl Ester | po | 800 | 1 | 4 | 5 |
|  | po |  | 1 | 2 | 3 |
| Dibutyl Ester | po | 800 | 0 | 0 | 0 |
| Dipentyl Ester | ip | 475 | 2 | 1 | 3 |
|  | po |  | 1 | 4 | 5 |
| Didecyl Ester | po |  | 0 | 1 | 1 |
| p-t-Butyl Deriv. | po | 125 | 0 | 1 | 1 |
| p-Hydroxy Deriv. | po | 400 | 0 | 1 | 1 |
| p-COOMe Deriv. | po | 750 | 0 | 2 | 2 |
| EHPG, Racemic isomer | ip | 125 | 3 | 5 | 8 |
| Meso Isomer | po | 75 | 1 | 0 | 1 |
| HBED | ip | 800 | 1 | 6 | 7 |
|  | po |  | 0 | 2 | 2 |
| HBED, Dipentyl Ester | ip |  | 1 | 4 | 5 |
|  | po |  | 2 | 9 | 11 |
| Dimethyl Ester | ip |  | 4 | 13 | 17 |
|  | po |  | 3 | 12 | 15 |
| HBPD | ip | 800 | 1 | 7 | 8 |
|  | po |  | 0 | 2 | 2 |
| HBPD, Dipentyl Ester | ip |  | 0 | 9 | 9 |
|  | po |  | 0 | 5 | 5 |
| HPHPD | ip | 800 | 1 | 8 | 9 |
|  | po |  | 0 | 1 | 1 |

*Dose of 100 mg/kg/day; Increments in urinary iron excretion relative to a control group are ranked as follows: 0 (0-50 μg/kg/day); 1 (50-200 μg/kg/day); 2 (200-350 μg/kg/day); 3 (350-500 μg/kg/day), etc. In a similar fashion, fecal iron excretion is ranked as follows: 0 (0-100 μg/kg/day); 1 (100-300 μg/kg/day); 2 (300-500 μg/kg/day); 3 (500-700 μg/kg/day); 4 (700-900 μg/kg/day); 5 (900-1100 μg/kg/day), etc.

Within the latter class a compound is identified which shows much greater activity than DFB in both the mouse and rat screens. This is N,N'-bis(2-hydroxybenzyl)ethylenediamine-N,N'-diacetic acid, HBED. This compound is hexadentate and its stability constant is among the highest known. It has an iron excretion ranking of 7 in the rat screen, compared with a value of 3 for DFB.

The HBED diester such as methyl was found to be about twice as active as the corresponding compounds of the HPBD series.

In the mouse infusion screen, the mouse is infused with a drug after its transfusions are complete and efficacy is based on percent iron depleted from the liver and spleen plus urinary iron excretion.

In the formulas above, I, II, and III, the product may be utilized as the mineral acid addition salts such as by utilizing sulfuric, hydrochloric, nitric or phosphoric acid.

In addition, due to the esterifying alcohol, the alkyl group in the ester is from 1-12 carbon atoms; they may be straight chain or branched chain. The alkyl radical forming the ester may be lower-alkyl, straight or branched chain representing 1-6 carbon atoms such as methyl, ethyl, N-propyl, isopropyl, isobutyl, N-butyl, secondary butyl, or tertiary butyl, as well as alkyl radicals having a carbon chain of 7-12 carbon atoms in analogous relationship.

I claim:

1. Iron chelators which are orally effective selected from straight and branched chain alkyl diesters and mineral acid addition salts of bis(2-hydroxy-aryl-(alkylenediamine)-dicarboxylic acids according to the following formulae:

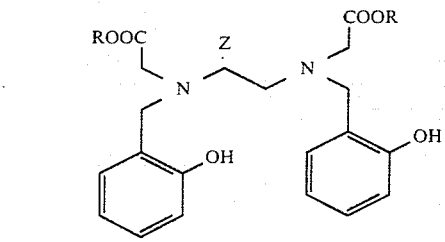

N,N'—bis(2-hydroxybenzyl)ethylenediamine-N,N—diacetic acid

R = methyl
Z = zero or a mineral acid addition salt selected from $H_2SO_4$, HCl, $HNO_3$, and $H_3PO_4$ active orally in mammals in dosages of 50–100 mg/kg/day to chelate and reduce iron overload in the plasma system.

2. Iron chelators according to claim 1 wherein the iron chelators are orally active in an animal selected from the group consisting of rats and mice.

3. A method of alleviating iron overload in plasma which comprises treating orally or I.P. a mammal with 50–100 mg/kg/day of a compound selected from one member of the group consisting of

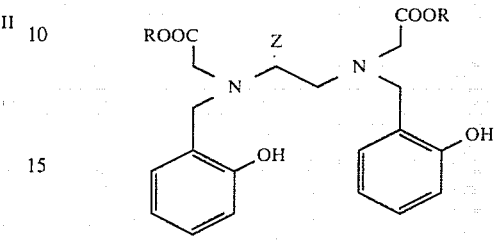

N,N'—bis(2-hydroxybenzyl)ethylenediamine-N,N—diacetic acid

R = methyl
Z = zero or a mineral acid addition salt selected from $H_2SO_4$, HCl, $HNO_3$, and $H_3PO_4$.

4. A method according to claim 3 wherein said method is used in treating a laboratory animal.

5. A method according to claim 3 wherein said method is used in treating an animal selected from the group consisting of rats and mice.

* * * * *